United States Patent
Bae et al.

(10) Patent No.: US 8,747,412 B2
(45) Date of Patent: Jun. 10, 2014

(54) SYSTEM AND METHOD FOR BONE ANCHOR REMOVAL

(75) Inventors: Hyun Bae, Santa Monica, CA (US); Edwin Su, New York, NY (US); Neil Etherington, North Logan, UT (US); Carlyle Creger, Wellsville, UT (US); Nathan Erickson, Beaver Dam, UT (US); Andrew Fauth, River Heights, UT (US)

(73) Assignees: IMDS Corporation, Providence, UT (US); Hyun Bae, Santa Monica, CA (US); Edwin Su, New York, NY (US)

( * ) Notice: Subject to any disclaimer, the term of this patent is extended or adjusted under 35 U.S.C. 154(b) by 179 days.

(21) Appl. No.: 13/396,349

(22) Filed: Feb. 14, 2012

(65) Prior Publication Data

US 2012/0239098 A1    Sep. 20, 2012

Related U.S. Application Data

(60) Provisional application No. 61/442,581, filed on Feb. 14, 2011, provisional application No. 61/496,659, filed on Jun. 14, 2011.

(51) Int. Cl.
| | | |
|---|---|---|
| *A61B 17/58* | (2006.01) | |
| *A61B 17/60* | (2006.01) | |
| *A61F 2/00* | (2006.01) | |
| *A61F 2/46* | (2006.01) | |
| *A61F 2/44* | (2006.01) | |
| *A61B 17/70* | (2006.01) | |

(52) U.S. Cl.
USPC ...... 606/104; 606/86 R; 606/86 A; 623/17.11

(58) Field of Classification Search
CPC .................................................. A61B 17/3468
USPC ............ 606/86 A, 86 R, 104, 138, 914, 916; 623/17.11
See application file for complete search history.

(56) References Cited

U.S. PATENT DOCUMENTS

| | | | |
|---|---|---|---|
| 6,447,546 | B1 * | 9/2002 | Bramlet et al. ............. 623/17.16 |
| 6,599,294 | B2 | 7/2003 | Fuss |
| 7,909,871 | B2 | 3/2011 | Abdou |
| 8,123,757 | B2 | 2/2012 | Zalenski |
| 8,491,598 | B2 * | 7/2013 | Crook .............................. 606/99 |
| 8,500,747 | B2 * | 8/2013 | DeRidder et al. ............... 606/99 |
| 2001/0037154 | A1 | 11/2001 | Martin |
| 2005/0055031 | A1 | 3/2005 | Lim |
| 2012/0253406 | A1 * | 10/2012 | Bae et al. ....................... 606/279 |
| 2012/0265259 | A1 * | 10/2012 | LaPosta et al. ............. 606/86 A |
| 2013/0013006 | A1 * | 1/2013 | Rashbaum et al. ......... 606/86 A |

FOREIGN PATENT DOCUMENTS

WO    WO2010121002    10/2010

* cited by examiner

*Primary Examiner* — Michael T Schaper
*Assistant Examiner* — David Bates
(74) *Attorney, Agent, or Firm* — Peter K. Johnson

(57) ABSTRACT

Systems and methods for bone anchor removal include a removal guide and a removal instrument. The removal guide includes grooves for guiding the removal instrument to the anchors, and for guiding removal of the anchor. The removal instrument includes a distal working end with a grasping feature designed to engage a portion of the bone anchor and an engagement feature designed to engage the grooves of the removal guide for anchor removal.

15 Claims, 10 Drawing Sheets

SYSTEM AND METHOD FOR BONE ANCHOR REMOVAL

CROSS-REFERENCE TO RELATED APPLICATIONS

This application claims the benefit of:

U.S. Provisional Patent Application No. 61/442,581, filed Feb. 14, 2011, entitled INSTRUMENT FOR ANCHOR REMOVAL; and U.S. Provisional Patent Application No. 61/496,659, filed Jun. 14, 2011, entitled INSTRUMENTATION AND METHODS FOR BONE ANCHOR REMOVAL.

The above referenced documents are hereby incorporated by reference in their entirety.

U.S. patent application Ser. No. 12/640,892, filed Dec. 17, 2009, entitled INTERVERTEBRAL IMPLANT WITH INTEGRATED FIXATION, is incorporated herein in its entirety.

BACKGROUND OF THE INVENTION

This disclosure relates to systems and methods for removing a bone fixation element, such as a bone anchor, from an implant. Specifically, this disclosure relates to a knee tibial prosthesis with a bicondylar tibial component and fixation elements. While the examples in the present disclosure relate to the knee joint, the systems and methods are applicable to other synovial joints in the body.

BRIEF DESCRIPTION OF THE DRAWINGS

Various examples of the present technology will now be discussed with reference to the appended drawings. It is appreciated that these drawings depict only typical examples of the invention and are therefore not to be considered limiting of its scope.

DETAILED DESCRIPTION

In this specification, standard medical directional terms are employed with their ordinary and customary meanings. Superior means toward the head. Inferior means away from the head. Anterior means toward the front. Posterior means toward the back. Medial means toward the midline, or plane of bilateral symmetry, of the body. Lateral means away from the midline of the body. Proximal means toward the trunk of the body. Distal means away from the trunk.

In this specification, a standard system of three mutually perpendicular reference planes is employed. A sagittal plane divides a body into bilaterally symmetric right and left portions. A coronal plane divides a body into anterior and posterior portions. A transverse plane divides a body into superior and inferior portions.

In this specification, standard knee anatomical terms are employed with their ordinary and customary meanings.

The present disclosure relates to systems and method for bone anchor removal. The bone anchors may be fixation elements that secure a prosthesis to a bone. An example of a joint arthroplasty system with bone anchors may include a prosthetic articular surface which replaces at least a portion of a natural articular surface of a bone, and a prosthetic component including a bone contacting surface. The bone contacting surface may include a means for attaching an anchor with a bladed fixation face and a rail portion. The system for bone anchor removal may include an anchor removal guide, shaped to be attached to a prosthesis, and a bone anchor removal instrument.

The systems and methods used for bone anchor removal will be discussed in the context of bone anchors coupled to a tibial tray component of a knee prosthesis, however, it is contemplated that the disclosed systems and methods for bone anchor removal, or adaptations thereof, may be used in other applications.

Figure 1:
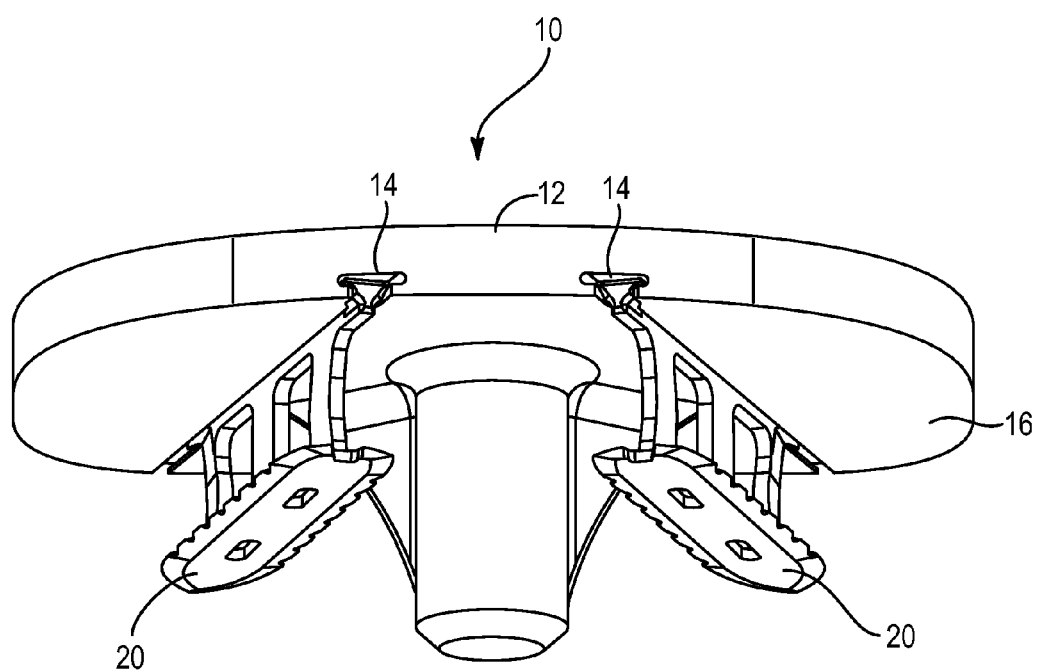
FIG. 1 is a bottom perspective view of a knee tibial prosthesis with a bicondylar tibial component and fixation elements.

The tibial tray may include at least one anchor. Referring to FIG. 1, a tibial tray prosthesis 10 is illustrated with two attached anchors 20. The anchors 20 may be parallel or angled relative to one another and/or the tray. For example, the anchors 20 of FIG. 1 are angled relative to one another, with the anchors 20 closest together at an anterior edge 12. The tibial tray 10 may have a posterior edge 13 that is opposite to the anterior edge 12. The anchors 20 may be inserted from the anterior edge 12 of the tibial tray 10 and may be oriented roughly anterior-posterior, as shown. The anchors 20 may be inserted into channels 14 on a bone-contacting surface 16 of the tibial tray 10. The channels 14 may be dovetailed as shown, or other undercut channel geometries may also be contemplated, such as T-slots.

The channels 14 of FIG. 1 extend between the anterior and posterior edges 12, 13 of the tray. In other examples, the channels 14 may only open at one of the anterior and posterior edges. In other examples, the channels 14 may be oriented exactly anterior-posterior, exactly medial-lateral, roughly medial-lateral, or in another orientation. A channel 14 may open through any perimeter edge of the bone-contacting surface 16 of the tibial tray.

The anchors 20 in the present disclosure may share some or all of the features of the anchors disclosed in U.S. patent application Ser. No. 12/640,892 to Bae, et al., which is incorporated herein by reference in its entirety.

Figure 2A:
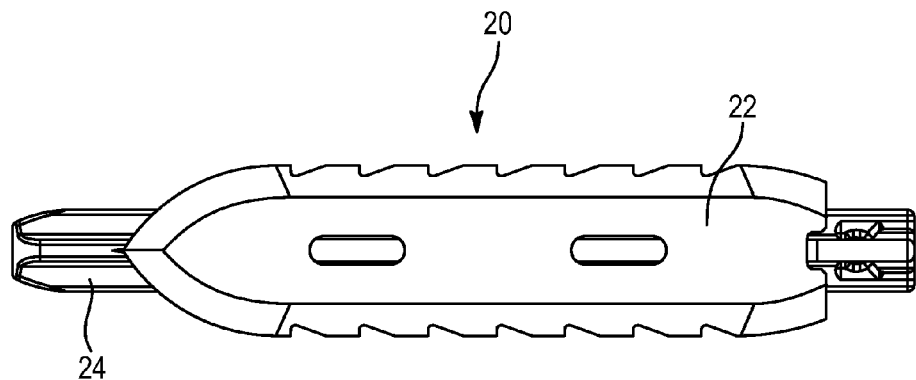
FIG. 2A is a bottom view of one of the fixation elements of FIG. 1.
Figure 2B:
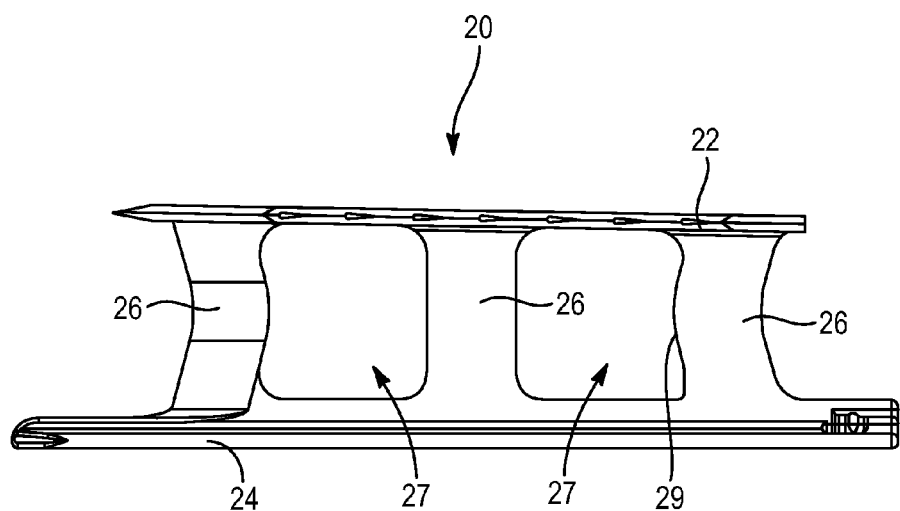
FIG. 2B is a side view of the fixation element of FIG. 2A.

Referring to FIGS. 2A and 2B, each anchor 20 may include a blade 22, which may also be referred to as a fin or a keel, and a rail 24. Supports, which may also be referred to as struts 26, may connect the blade to the rail, and may define at least one aperture 27, which may also be referred to as a window or a hole. Each aperture may be defined by at least one edge 29. The rail 24 may be shaped to be received within the channel 14 on the bone contacting surface 16.

Figure 3:
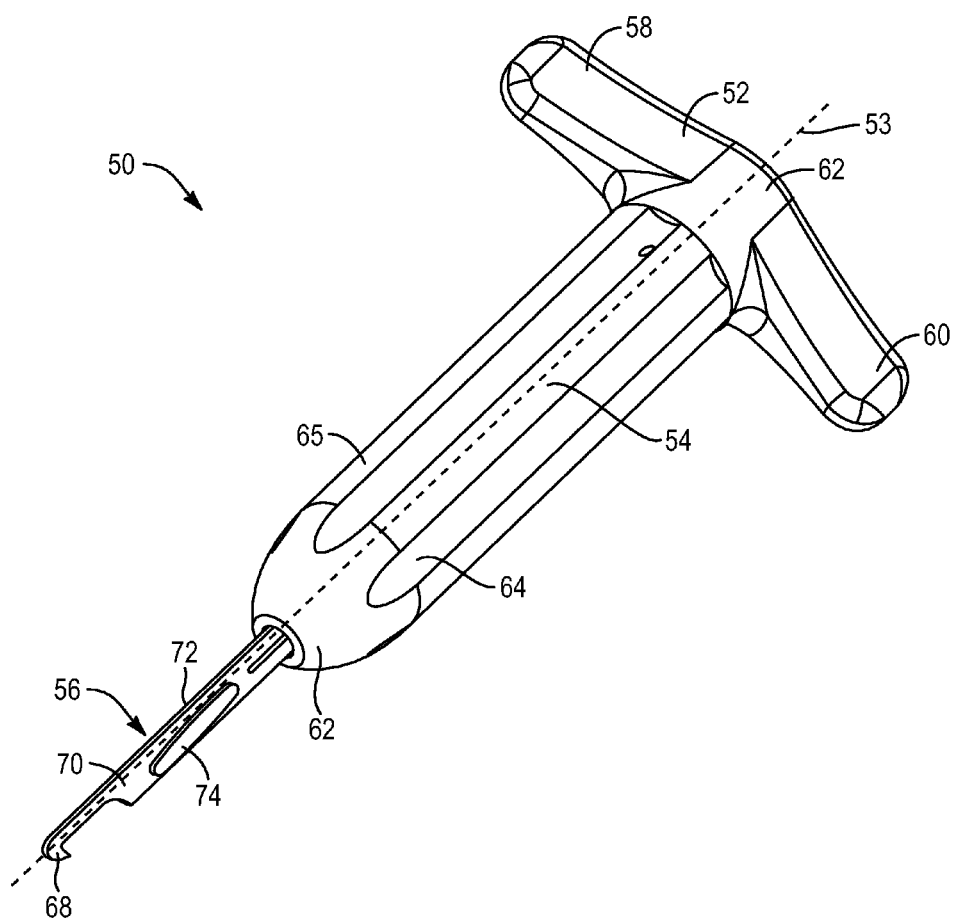
FIG. 3 is a side perspective view of a bone anchor removal instrument.

Referring to FIG. 3, an anchor removal instrument 50 may include a handle 52, a shaft 54 and a distally located working end 56. The instrument 50 may also include a central axis 53 that extends longitudinally through the shaft 54 and working end 56. The handle 52 may have a first arm 58 and a second arm 60 opposite the first arm 58. The first 58 and second arms 60 may intersect at a middle portion 62. The shaft 54 may be attached to the handle 52 at the middle portion 62 to form a T-handle, and may extend distally substantially perpendicular the handle 52. The two handle arms 58, 60 may extend away from each other at a slight angle, as illustrated in FIG. 3A, or may extend outward such that they are collinear to one another. The shape and orientation of the handle 52 may be variable and include exterior gripping features.

In another example of anchor removal instrument 50, the handle portion may be the termination of the shaft 54, and there may be no arms or other extending features.

The shaft 54 may extend between the handle portion 52 and the distal working end 56, and may be substantially cylindrical, with a rounded neck portion 62 that connects to the distal working end 56. The shaft 54 may include a series of surface indentations 64 that extend along the length of the shaft 54. The shaft 54 may include an exterior housing element 65 that is substantially hollow, or may completely solid.

Alternatively, the shaft 54 may be polygonal or irregularly shaped, and may include a smooth outer surface. The length and diameter of the shaft 54 may be variable.

The distal working 56 end may extend from the rounded neck portion 62. The distal working end 56 may be formed separately from the shaft 54 and may be attached to the shaft 54 via a snap or press fit, weld, threads, or other means. The distal working end 56 may otherwise be integrally formed with the housing of the shaft 54.

The distal working end 56 may include a hook 68 or other grasping feature. The distal working 56 end may be substantially flat, and contain a first face 70, and a second face 72 opposite the first face 70. At least one face may include a dovetail rocker feature 74 that may also be referred to as an engagement feature 74. The dovetail rocker feature may protrude outward from the corresponding face. The engagement feature 74 may alternatively be a rail or another shape.

Figure 4A:
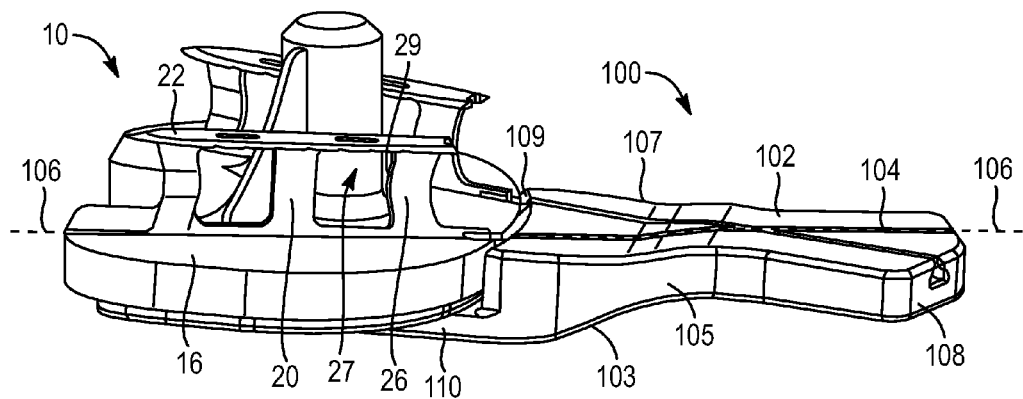
FIG. 4A is a side perspective view of the knee tibial prosthesis of FIG. 1 with an attached anchor removal guide.
Figure 4B:
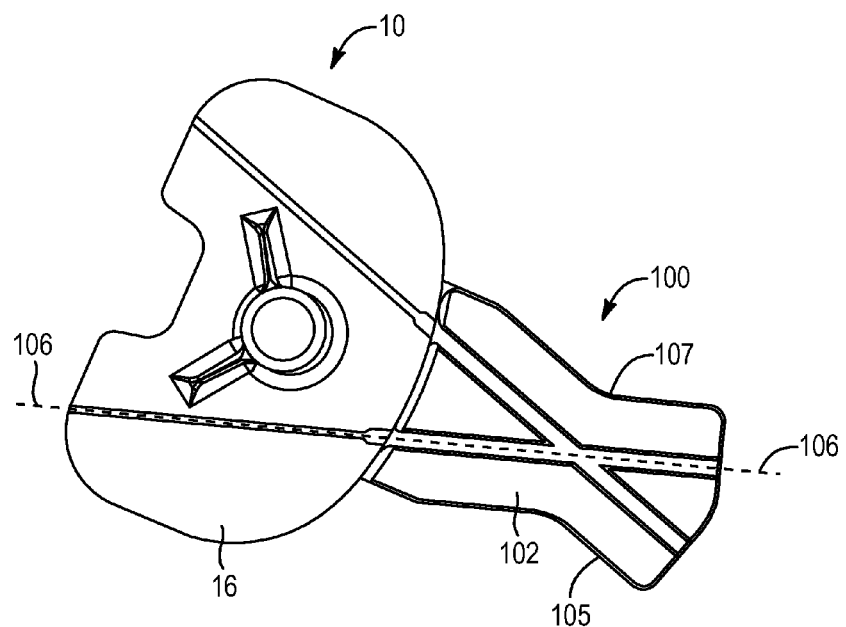
FIG. 4B is a bottom view of the knee tibial prosthesis and anchor removal guide of FIG. 4A with a bone anchor removal instrument, the fixation elements removed for clarity.

The anchor removal instrument 50 may be used in conjunction with an anchor removal guide. Referring to FIGS. 4A and 4B, a removal guide 100 is illustrated, attached to the anterior edge 12 of tibial tray prosthesis 10. In FIG. 4A, the prosthesis 10 is shown with installed anchors 20. In FIG. 4B, the prosthesis 10 is shown without anchors 20. The removal guide 100 may include a first surface 102, and a second surface 103 that is opposite to the first surface 102. The removal guide 100 may also include a side portion 105 that extends between the first surface 102 and the second surface 103, and a second side 107 that is opposite the first side portion 105. The removal guide may include an end surface 108 that extends between the first surface 102 and the second surface 103, and intersects the first side portion 105 and the second side portion 107. The first surface 102 may include at least one removal groove 104. Shown in FIG. 4, the first surface 102 contains two removal grooves that extend along the first surface 102 in an X-shape, intersecting at substantially their midpoints. The removal grooves 104 may have a complimentary dovetail shape to the engagement feature 74 on the distal working end 56 of removal instrument 50. The grooves 104 may also be shaped to receive the rail portion 24 of the anchors 20. The removal grooves 104 may intersect the end surface 108 and extend entirely across the first surface 102 to intersect a prosthesis-interface surface 109. The prosthesis-interface surface may also be referred to as a second end face 109, and may be contoured to match the curvature of a corresponding tibial tray 10 or other prosthetic member. The second end face 109 may extend from the first surface 102 substantially perpendicularly and intersect an extended portion 110 of the removal guide 100. The extended portion 110 is shaped to extend across a prosthetic face that is opposite to the bone-contacting face 16.

Prior to anchor removal, the removal guide 100 may be reversibly attached to the prosthesis 10 via a snap fit, press fit, or other reversible fit methods. Alternatively, the removal guide 100 may be connected independently to the bone. When the removal guide 100 is connected to the tibial tray 10, as illustrated in FIGS. 4A-B, at least one groove 104 on the first surface 102 may be coaxially aligned with one of the anchor channels 14 on the tibial tray. The axis along which the groove 104 and anchor channel 14 are coaxially aligned may be called a removal axis 106. The first surface 102 of the removal guide 100 may be coplanar with the bone-contacting surface 16 of the tibial tray 10, although uneven surfaces are also contemplated.

In addition to the first groove 104, a portion of the anchor channel 14 may also have a complimentary dovetail shape to the engagement feature 74 on the distal working end 56 of anchor removal instrument 50. It may be appreciated that in other embodiments of the invention, mating features on the anchor 20, tibial tray 10 and instrument 50 may not be dovetail shaped, but may instead be T-shaped or H-shaped complementary features, curved complimentary features, or other features that allow the anchor to slidingly engage and/or disengage with the tibial tray. Preferably, the sliding engagement features may include one or more undercuts or interdigitating features.

Figure 5:
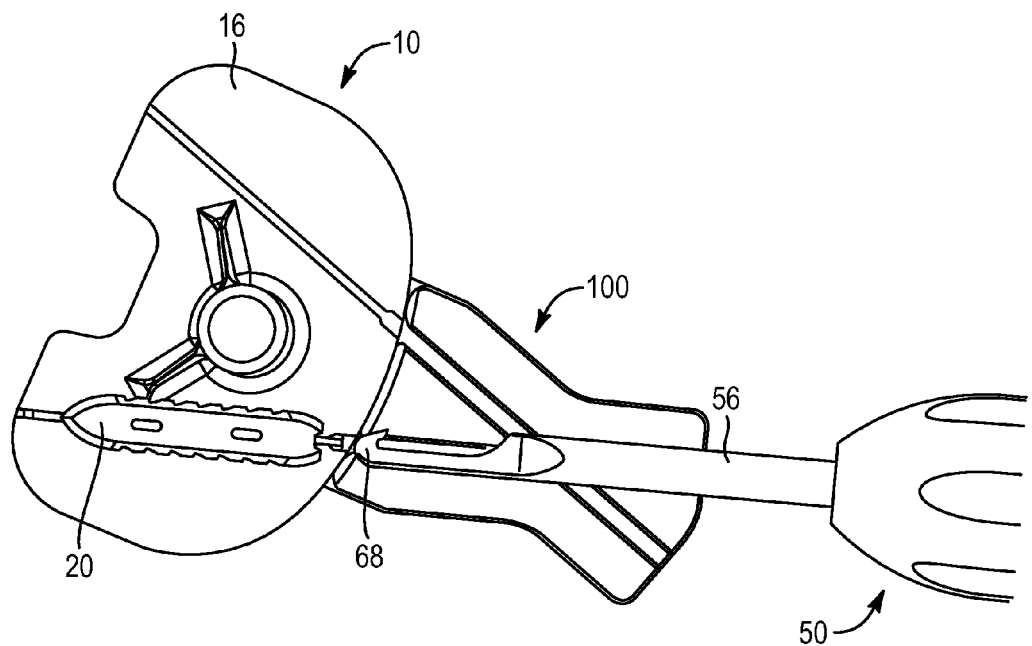
FIG. 5 is a bottom view of the knee tibial prosthesis, anchor removal guide, and bone anchor removal instrument of FIG. 4B, now showing a fixation element.
Figure 6:
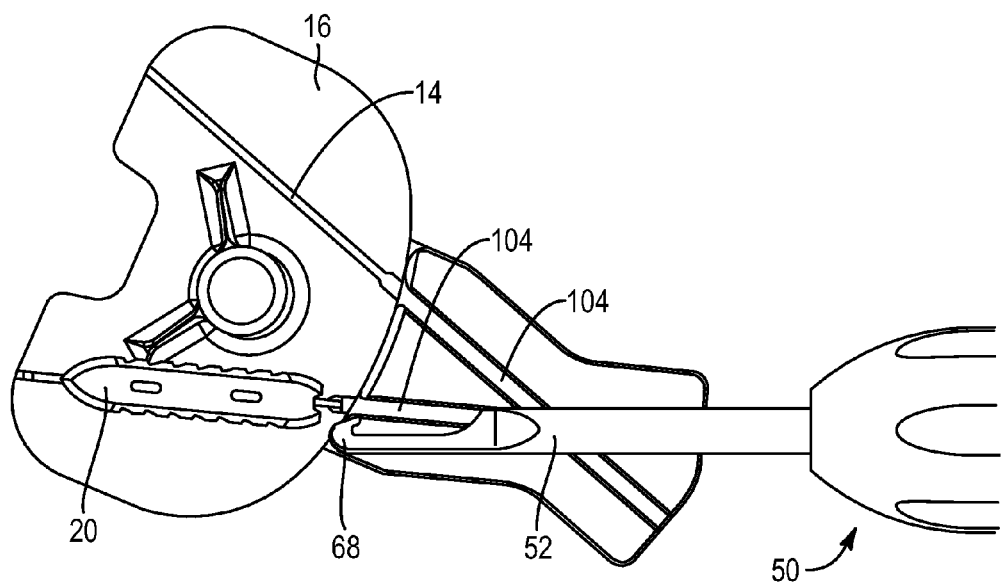
FIG. 6 is a bottom view of the knee tibial prosthesis, anchor removal guide, and bone anchor removal instrument of FIG. 5.

Referring to FIG. 5, to remove the bone anchor 20, the removal guide 100 may be attached to the tibial tray 10 or independently to the bone, such that the first groove 104 is coaxially aligned with a channel 14 on the bone-contacting surface 16 of the tibial tray 10, wherein the anchor 20 to be removed is attached in the channel 14. The instrument 50 may be positioned such that at least a portion of the dovetail rocker feature 74 is contained within the groove 104. The instrument 50 may then be advanced distally towards the anchor 20 in the groove 104, wherein the removal hook 68 is guided in the channel until the hook 68 contacts the support 26 of the anchor 20, as illustrated in FIG. 5. When the hook 68 contacts the support 26 of the anchor, further distal advancement may be prohibited or resisted. The dovetail rocker 74 may allow the instrument 50 to rotate in one direction, such that the distal hook 68 is off-alignment with the removal axis 106 as illustrated in FIG. 6, and the hook 68 is no longer in contact with the support 26. The instrument 50 may then be further advanced distally, and remains off-alignment with the removal axis 106, while the shaft 54 of the instrument remains aligned with the removal axis 106. Once the hook 68 has been driven sufficiently far, the dovetail rocker 74 may allow the hook 68 to realign to the removal axis 106 and engage the support by "hooking" the side of the support 29. The dovetail rocker 74 may allow for rotation of the working end 56 only in a first direction, and may prohibit rotation in a second direction. The dovetail rocker 74 may allow for rotation of the working end 56 away from the axis 106 to one side only, and back into alignment with the axis. Corresponding rotation to the other side of the axis 106 may be prohibited.

After the hook 68 has engaged a support structure 26 of the anchor 20, the anchor 20 may be removed by pulling the instrument 50, and attached anchor 20, proximally out of the tibial tray anchor channel along the removal axis 106.

Figure 7A:
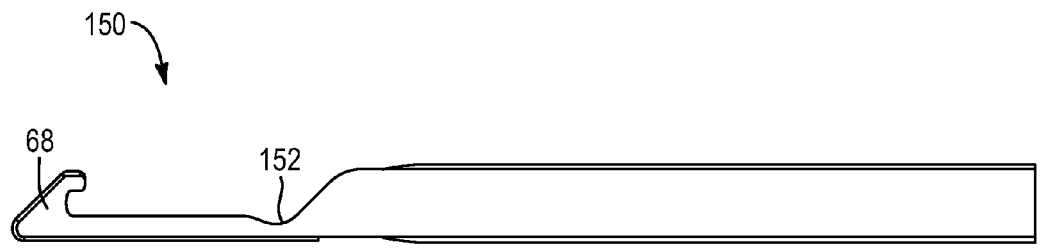
FIG. 7A is a side view of another bone anchor removal instrument.
Figure 7B:
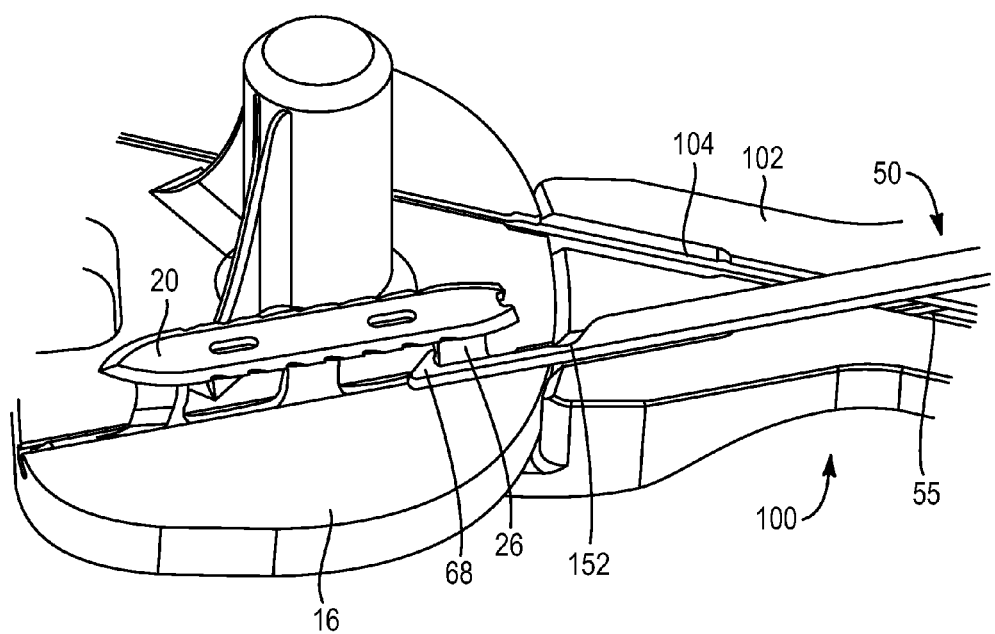
FIG. 7B is a bottom perspective view of the knee tibial prosthesis and anchor removal guide of FIG. 4A with the bone anchor removal instrument of FIG. 7A.

Referring to FIG. 7A, another example of a distal working end is shown. The shaft and handle (not shown in FIG. 7) may be similar to the shaft 54 and handle 52 of the previous example. Working end 150 includes a distal grasping feature 68, such as a hook, and a flexion notch 152. The flexion notch 152 may be cut into the distal working end 150, adjacent or proximal to the hook 68. The flexion notch 152 may act similar to the dovetail engagement feature 74 described in the previous example, and allow the working end 150 to flex or deflect to one side of the support 26 of the anchor as the instrument 50 is engaged distally in the groove 104. The flexion may be forced, such as by driving the instrument 50 forward with a mallet or a screw mechanism. In this example, the working end 150 may include a feature 55 which fits into and closely complements the groove 104 to align and stabilize the instrument 50 as it is advanced. Referring to FIG. 7B, an instrument 50 with working end 150 is shown engaged with a support 26 of an anchor 20, and the anchor 20 may be removed by pulling the instrument 50, and attached anchor 20, proximally along the removal axis 106.

Figure 8A:
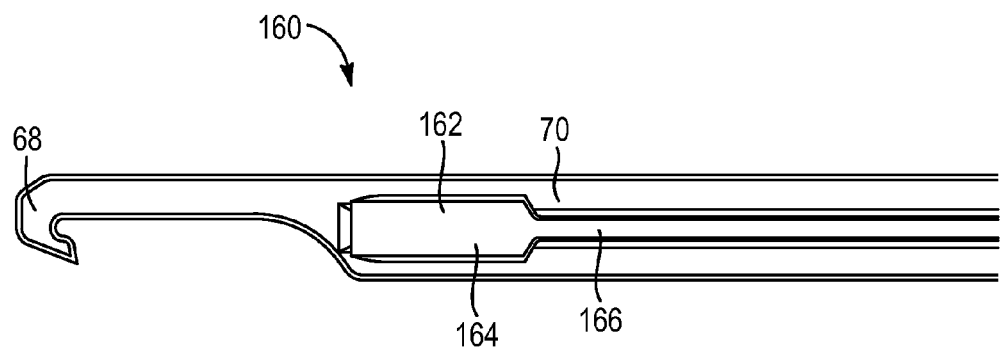
FIG. 8A is a side view of yet another bone anchor removal instrument.

Referring to FIG. 8A, another example of a distal working end is shown. The shaft 54 and handle 52 (not shown in FIG. 8) may be similar to those described previously. Alternatively, as illustrated in FIG. 8B, the shaft 54 may be a rod-like structure that extends proximally from the distal working end 56, and does not include a housing element.

Distal working end 160 includes a grasping feature 68, such as a hook, and a protruding engagement portion 162. Protruding engagement portion 162 may extend from the first face 70 of the distal working end, and may include a block portion 164 and a rail 166.

The instrument 50 with working end 160 may be inserted freehand, or unguided, at a downward or other selected angle until it makes contact with a support structure 26 of the anchor 20. The hook 68, located on the distal working end 56, may engage the support 26 of the anchor when at least a portion of the hook 68 is inserted into the aperture 27 of the anchor 20 and is secured to an inside surface 29 of the aperture 27. The grasping feature 68 may otherwise engage another feature of the anchor 20.

Figure 8B:
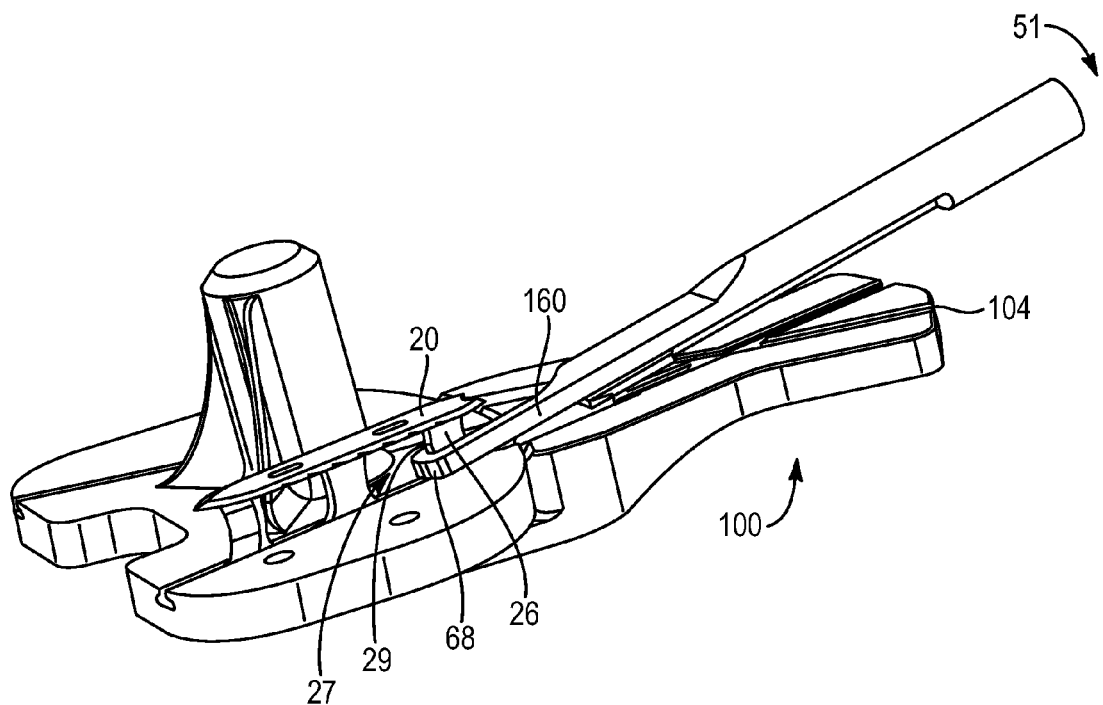
FIG. 8B is a bottom perspective view of the knee tibial prosthesis and anchor removal guide of FIG. 4A with the bone anchor removal instrument of FIG. 8A.
Figure 8C:
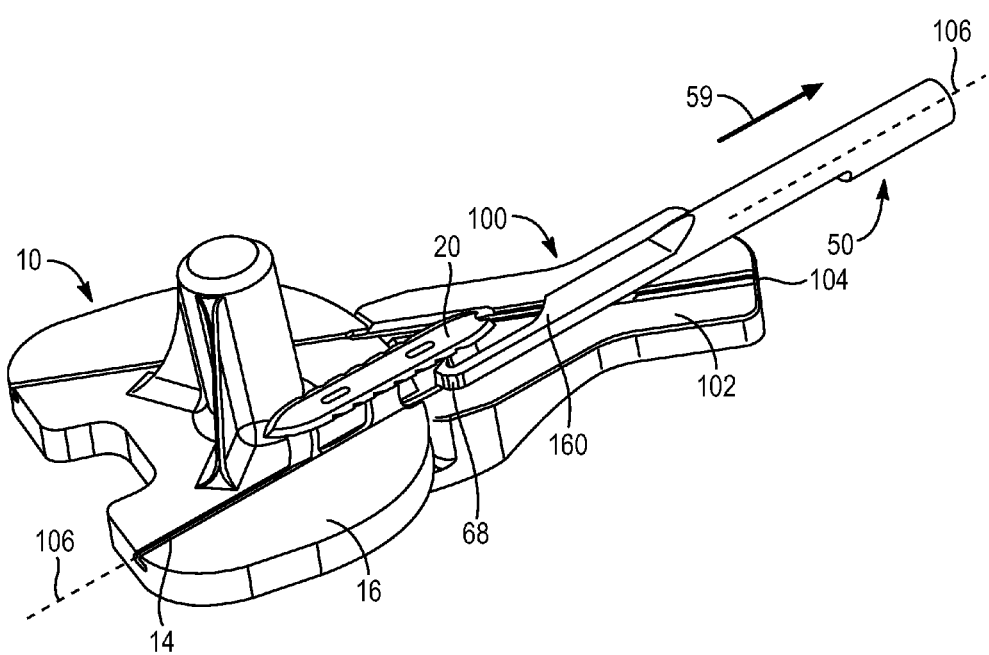
FIG. 8C is a bottom perspective view of the knee tibial prosthesis, anchor removal guide, and bone anchor removal instrument of FIG. 8B engaged with a bone fixation element.

Upon engagement with support 26, the instrument 50 may then be maneuvered so that the protruding engagement feature 162 of the anchor removal instrument 50 couples or engages with first groove 104 on the removal guide 50, as shown by the motion arrow 51 in FIG. 8B. When protruding engagement feature 162 is coupled to the first groove 104, at least a portion of protruding engagement feature 162 is contained within the groove 104. Once the engagement feature 162 has engaged with the complementary portion of the first groove 104, as illustrated in FIG. 8C, the instrument 50 may lie substantially parallel to the plane of the first surface 102, and the instrument 50 may be actuated to remove the anchor 20 from engagement with the tibial tray 10 and adjacent bone. The anchor 20 may be removed by pulling the instrument 50, and attached anchor 20, proximally out of the tibial tray anchor channel along the removal axis 106, as shown by the motion arrow 59 in FIG. 8C.

Figure 9A:
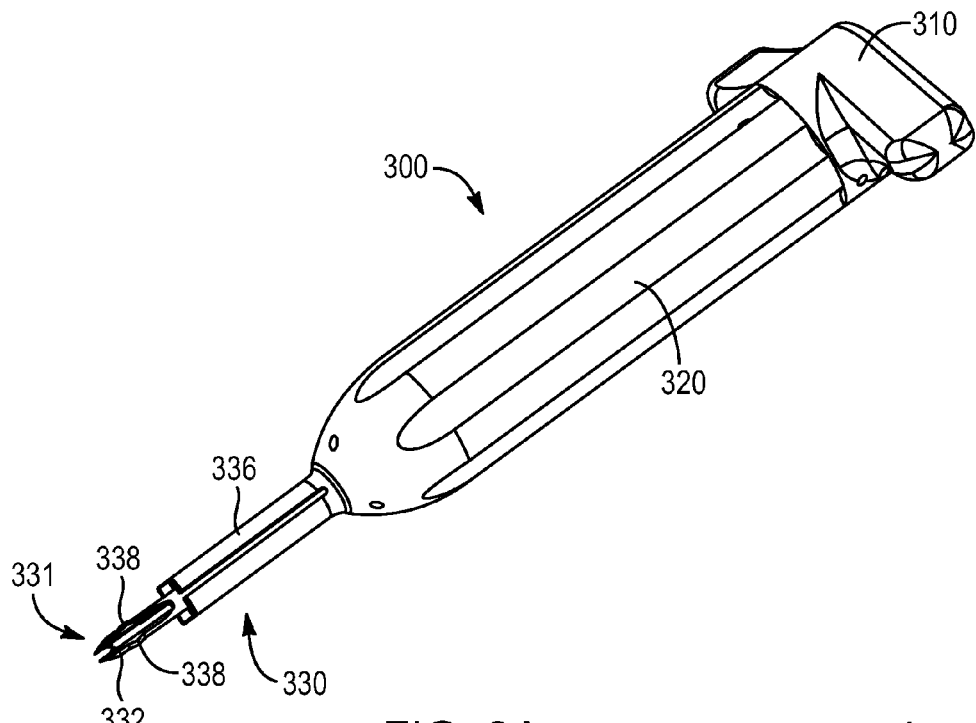
FIG. 9A is a perspective view of yet another bone removal instrument.
Figure 9B:
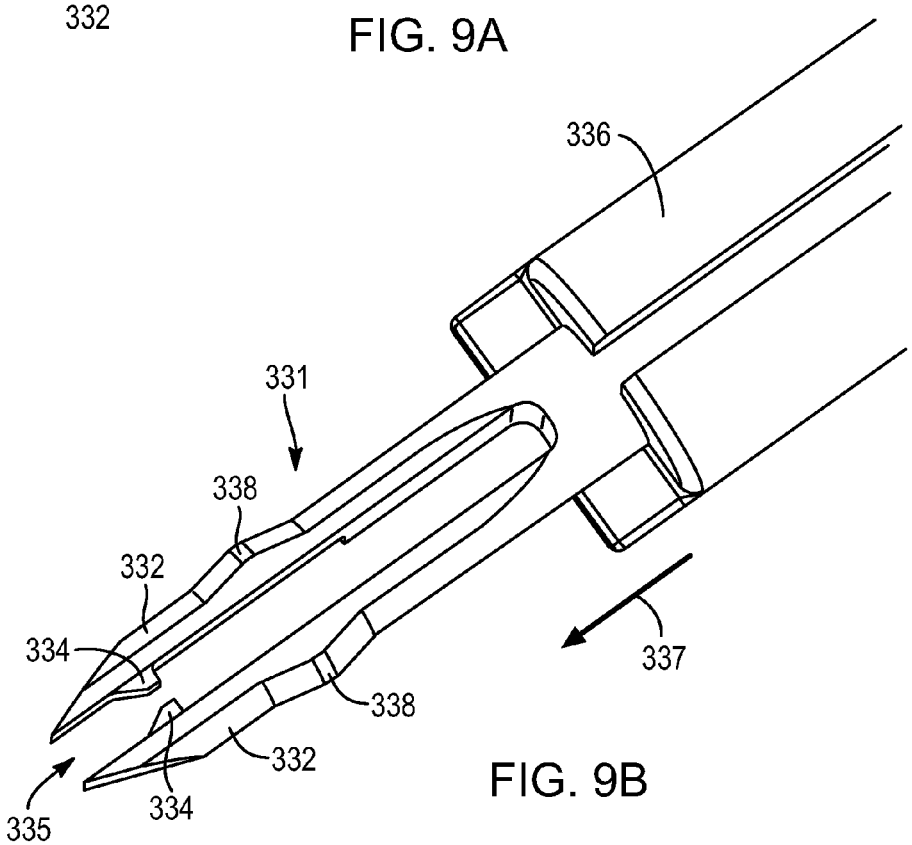
FIG. 9B is an enlarged detail view of a distal working end of the bone anchor removal instrument of FIG. 9A.

Referring to FIGS. 9A-9B, an example of an anchor removal instrument 300 with an alternative distal working end is shown. Anchor removal instrument 300 includes an actuation handle 310, a shaft 320 and a distally located working end 330. The actuation handle 310 may have a structure similar to handle 52 described previously. The shaft 320 may extend substantially perpendicular to the handle 310, and have a similar structure to shaft 54 described previously.

The distally located working end 330 may include a compression sleeve 336, and a split chisel 331. The compression sleeve 336 may be located between the split chisel 331 and the distal end of the shaft 320. The compression sleeve 336 may be a tubular component that encompasses a proximal portion of the distal working end 330, and may be slidable along the length of the working end 330.

The split chisel 331 may extend distally from the compression sleeve and may include chisel tips 332, compression tabs 338 and engagement bosses 334. The compression tabs may be located on the exterior side of the chisel tips 332, and the engagement bosses 334 may be located at the distal end on the interior side of the chisel tips 332.

To engage the anchor 20 for removal, the split chisel 331 may be malleted into the bone such that the support 26 of the anchor 20 is located in the space 335 between the chisel tips 332, and such that the engagement bosses extend at least partially into the aperture 27. The compression sleeve 336 may be advanced over the chisel tips 332, as indicated by motion arrow 337 in FIG. 9B. The advancement of the compression sleeve 336 may be accomplished by turning the handle 310 relative to the shaft 320 to drive the compression sleeve 336 forward. As the compression sleeve 336 contacts the compression tabs 338, the chisel tips are urged toward one another, and the anchor engagement bosses 334 may be urged farther into the aperture 27 on the anchor, and may close around the anchor support 26 or other feature on the anchor 20. Once the chisel tips 332 have engaged the anchor 20, further rotation of handle 310 may urge extraction of the anchor as it is drawn toward shaft 320. In this embodiment, the instrument may be inserted unguided and upon engagement with the anchor element may also be removed unguided. Alternatively, once the chisel tips 332 have engaged the anchor 20, the instrument 300 may be pulled proximally along the removal axis to remove the anchor 20.

Another embodiment of a pinching removal instrument 300 may include a guiding engagement feature such as the protruding engagement feature 162 or the dovetail rocker feature 74 such that the instrument can be guided along the removal axis 106 by the groove 104 and the channel 14 to engage the anchor 20 and/or to remove the anchor 20.

The compression of the chisel tips 332 towards one another with the advancement of the compression sleeve 334 may be used to unlock a spring mechanism, or other similar locking feature simultaneously as it engages the removal feature on the anchor and begins to extract it.

Figure 10A:
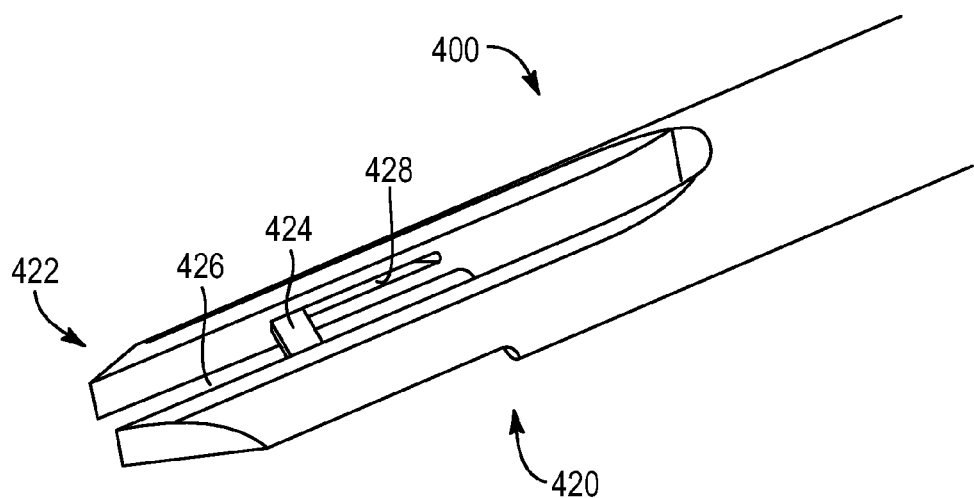
FIG. 10A is a perspective view of yet another bone removal instrument.
Figure 10B:
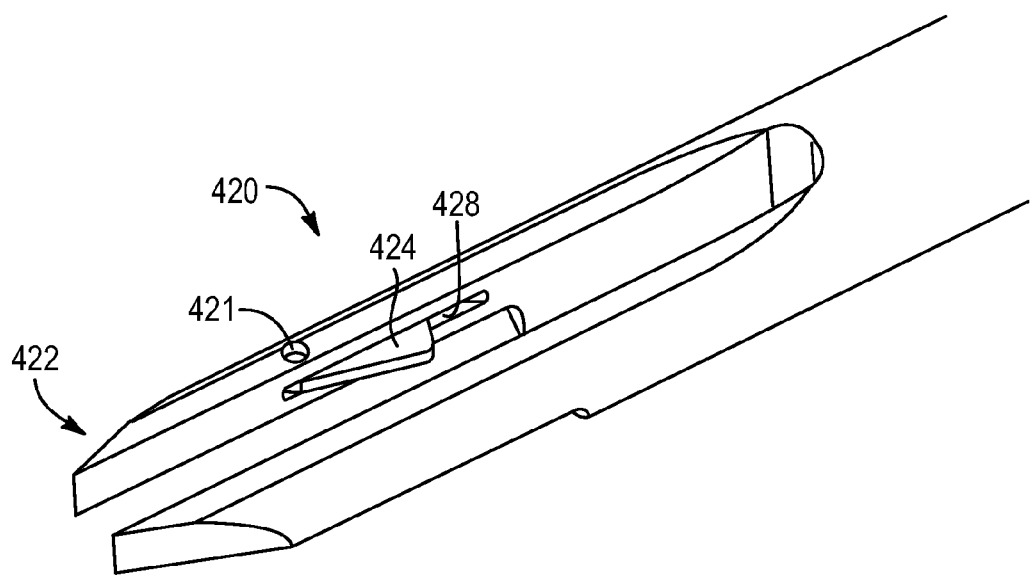
FIG. 10B is an enlarged detail view of a distal working end of the bone anchor removal instrument of FIG. 10A.

Referring to FIGS. 10A and 10B, another embodiment of an anchor removal instrument is shown. The instrument 400 includes an actuation handle (not shown in the figures), a shaft 412 and a distally located working end 420 comprising a split chisel 422 and a spring latch 424. The spring latch may be positioned in a "neutral" or "closed" position, in which the latch arm 424 extends across the channel 426 between the chisel tips 422 as shown in FIG. 10A. The spring latch may be of a variety of shapes, and can be a pinned, pivoting interface, or it may be a solid metal interface that may deflect out of the way into an "open position". The spring latch 424 may be spring biased towards the neutral position, and may be transitionable to the open or deflected position as illustrated in FIG. 10B, in which the spring latch arm 424 becomes at least partially contained within a spring latch recess 428, located on the interior side of the chisel tips 422. The spring latch arm 424 may rotate about a spring latch pivot 421 that lies on an axis normal to the plane of the spring latch arm 424.

To engage the anchor 20 for removal, the instrument may be malletted into the bone such that the anchor support 26 is positioned between the chisel tips 422 and contacts the spring latch 424. The instrument 400 may be advanced forward such that the spring bias is overcome and the spring latch 424 is pushed into the deflected position. Once the spring latch 424 has cleared the anchor support 26, it may swing closed, either passively or via an active mechanical closure system to lockably engage the anchor support 26.

Upon closure, the spring latch 424 contacts a stop on the opposite site from the spring latch pivot, which may prevent the latch from opening during removal of the anchor. One the latch has engaged the stop, the instrument can be twisted and/or pulled to remove the anchor.

It will be appreciated that any of the designs and concepts contemplated herein can be mixed and matched to form alternate embodiments. The designs and concepts presented herein may be applied to other orthopedic anchors, devices and implants. These devices may have uses in other orthopedic joints and procedures.

The invention claimed is:

1. A system for removal of an anchor from an implant, the system comprising:
   an anchor;
   an implant, wherein the implant has a channel, wherein the anchor is at least partially contained within the channel and capable of protruding from the implant to secure the implant to a bone when fully seated within the channel;
   a removal guide, wherein the removal guide comprises a first surface having a groove, wherein the removal guide is positionable such that the groove is coaxially aligned with the channel, wherein when the groove is coaxially aligned with the channel, the groove and the channel define a removal axis; and
   an instrument, the instrument comprising a body, wherein the body comprises a central axis and a working end, wherein the working end comprises a grasping feature and an engagement feature, the grasping feature adapted to engage a support of the anchor, wherein the grasping feature is adapted to be off-alignment with the removal axis when the groove and the channel define the removal axis, and wherein the engagement feature is adapted to engage the groove and wherein the groove is shaped to receive at least a portion of the engagement feature such that a force may be applied by the instrument to the anchor to remove the anchor from the implant along the removal axis.

2. The system of claim 1, wherein the engagement feature is a dovetail.

3. The system of claim 1, wherein the grasping feature comprises a hook.

4. The system of claim 3, wherein when the hook engages the support of the anchor, the engagement feature can engage the groove.

5. The system of claim 4, wherein when the engagement feature engages the groove, at least a portion of the engagement feature is contained within the groove, wherein when a portion of the engagement feature is contained within the groove, the central axis of the body is parallel to the removal axis.

6. The system of claim 5, wherein when the engagement feature engages the groove, the anchor is slidably removable from the implant along the removal axis.

7. A system for removal of an anchor from an implant, the system comprising:
   an anchor;
   an implant, the implant having a channel, the anchor at least partially contained within the channel and capable of protruding from the implant to secure the implant to a bone when fully seated within the channel;
   a removal guide, wherein the removal guide comprises a first surface, wherein the first surface comprises a groove, wherein the removal guide is positionable such that the groove is coaxially aligned with the channel, wherein when the groove is coaxially aligned with the channel, the groove and the channel define a removal axis; and
   an instrument, the instrument comprising a handle and a working end opposite the handle, the working end comprising a grasping feature and an engagement feature, wherein the grasping feature is adapted to engage a support structure of the anchor, wherein the engagement feature is adapted to engage the groove and wherein the groove is shaped to receive at least a portion of the engagement feature such that a force may be applied by the instrument to the anchor to remove the anchor from the implant along the removal axis, and wherein the working end is pivotable relative to the removal axis between a first alignment and a second alignment which extends on an axis other than the removal axis when the groove and the channel define the removal axis and the engagement feature is engaged with the groove.

8. The system of claim 7, wherein when the working end is in a first alignment, the working end is coaxially aligned with the removal axis.

9. The system of claim 7, wherein when the working end is in a second alignment, the working end is off-axis from the removal axis.

10. The system of claim 7, wherein the engagement feature is a rocker that is adapted to engage the channel, and wherein the rocker comprises a dovetail.

11. The system of claim 10, wherein the working end is shaped to be inserted into the groove and further into the channel along the removal axis.

12. The system of claim 11, wherein when the working end is inserted a first distance into the channel, the dovetail contacts a portion of the support, and further insertion is resisted by the support.

13. The system of claim 12, wherein when further insertion is resisted, the working end moves from the first alignment to the second alignment.

14. The system of claim 12, wherein when the working end moves to the second alignment, the resistance to further insertion is overcome and the working end is moved further into the channel, such that when the working end is moved further into the channel, the grasping feature engages the support of the anchor.

15. The system of claim 14, wherein when the grasping feature engages the support of the anchor, the anchor may be removed by pulling the anchor along the removal axis.

* * * * *